United States Patent [19]

Au et al.

[11] Patent Number: 5,217,886
[45] Date of Patent: Jun. 8, 1993

[54] METHOD FOR THE PRODUCTION OF (−)-4-DIFLUOROMETHYL-ORNITHINE

[75] Inventors: Andrew T. Au, Sugarland, Tex.; Nancy L. Boardway, South Hampton, Mass.

[73] Assignee: Merrell Dow Pharmaceuticals Inc., Cincinnati, Ohio

[21] Appl. No.: 722,042

[22] Filed: Jun. 27, 1991

Related U.S. Application Data

[63] Continuation-in-part of Ser. No. 238,936, Aug. 31, 1988, abandoned.

[51] Int. Cl.$^5$ .................... C12P 13/00; C12P 13/08; C12P 13/10; C12N 9/14
[52] U.S. Cl. .................... 435/128; 435/106; 435/115; 435/195; 435/114
[58] Field of Search ............... 435/128, 106, 115, 195, 435/114

[56] References Cited

FOREIGN PATENT DOCUMENTS 9062684 6/1974 Japan.

OTHER PUBLICATIONS

T. Fukumura, *Plant & Cell Physiol* vol. 18, pp. 1173–1176, (1977).
K. Plhackova et al., *Folia Microbiol* 27, pp. 382–389 (1982).
T. Fukumura et al., *FEBS Letters* vol. 89, pp. 298–300 (1978).

*Primary Examiner*—Irene Marx
*Attorney, Agent, or Firm*—Michael J. Sayles

[57] ABSTRACT

The present invention is directed to a process for producing (−) 2-substituted-ornithines comprising contacting a 2-substituted-piperidone with L-α-E-aminocaprolactam-hydrolas in the presence of a divalent cation.

4 Claims, No Drawings

METHOD FOR THE PRODUCTION OF (−)-4-DIFLUOROMETHYL-ORNITHINE

This is a continuation-in part of application Ser. No. 07/238,936, filed Aug. 31, 1988 now abandoned.

BACKGROUND OF THE INVENTION

The present invention is directed to a method for the production of the (−) optical isomer of 2-substituted-ornithines.

2-Substituted-ornithines such as α-difluoromethylornithine have been reported to be inhibitors of the enzyme, ornithine decarboxylase, (J. Org. Chem., Vol. 44, No. 15, Bey, et al. (1979)). They have been reported to be useful in the treatment a number of disease states such as for example, psoriasis, benign prostatic hypertrophy, and as an antineoplastic agent, U.S. Pat. Nos. 4,743,691 and 4,496,588.

U.S. Pat. No. 4,496,588 teaches a method for resolving the optical isomers of these 2-substituted ornithines. The process comprises resolving a racemic 2-piperidone of the structure:

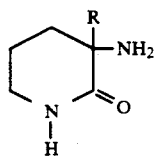

wherein R represents the desired halogenated methyl radical, with (−) binaphthylphosphoric acid. Each of the optical isomers of the piperidone are then hydrolyzed separately to produce the desired optical isomer of the 2-substituted-ornithine.

Thus it would be a valuable contribution to the art to develop a process wherein the piperidone could be hydrolyzed and resolved in one step.

SUMMARY OF THE INVENTION

In accordance with the present invention it has been discovered that the (−) optical isomers of 2-substituted-ornithines can be produced by contacting a 2-substituted-piperidone with L-α-amino-E-caprolactam hydrolase in the presence of a divalent cation.

DETAILED DESCRIPTION OF THE INVENTION

As used in this application:

a) the term halogen refers to a fluorine, chlorine or bromine atom;

b) the term $C_{1-4}$ alkyl group refers to a branched straight chain alkyl group containing from 1–4 carbon atoms, such as methyl, ethyl, n-propyl, isopropyl, n-butyl and isobutyl;

c) the term $C_{1-4}$ alkoxy group refers to a straight or branched alkoxy group containing from 1–4 carbon atoms, such as methoxy, ethoxy, n-propoxy, isopropoxy, n-butoxy and isobutoxy;

d) the term halogenated $C_{1-4}$ alkyl refers to a straight or branched alkyl group containing from 1–4 carbon atoms which is substituted with one or more halogen atoms. Any of the carbon atoms within the alkyl group may be substituted with up to 2 or 3 halogen atoms depending upon its location with the alkyl group. Representative examples of halogenated $C_{1-4}$ alkyl's include difluoromethyl, trifluoromethyl, and 1-chloro-3-fluoro-n-butyl;

e) the formula $C_6H_5$ refers to a phenyl ring;

f) the term hydroxylated $C_{1-4}$ alkyl refers to a straight or branched alkyl group containing from 1–4 carbon atoms which is substituted with one or more hydroxyl functions. The hydroxyl function may be located on any of the carbon atoms within the alkyl group and a single carbon atom should not be substituted with more than one hydroxyl function;

g) the term ether refers to one of the following substituents: $(CH_2)_nO(CH_2)_m$ or $(CH_2)_nOC_6H_5$, wherein n and m are each independently represented by the integers 1 or 2;

h) the term phenoxy refers to the following substituent: $OC_6H_5$;

i) the term divalent cation refers to a positively charged ion having a valence of +2;

j) the symbol (−) refers to those enantiomers which rotate polarized light to the left, and may also be referred to as the (l) isomer;

k) the symbol (+) refers to those enantiomers which rotate polarized light to the right, and may also be referred to a the (d) isomer, and;

m) the term racemic refers to a sample which contains both the (+) and (−) isomers.

The (−) 2-substituted-ornithines which can be produced by the process of the present invention can be represented by the following formula:

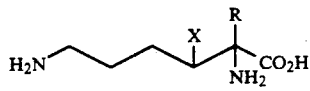

FORMULA I wherein R is selected from the group consisting of a $C_{1-4}$ alkyl, a $C_{1-4}$ alkoxy, a halogenated $C_{1-4}$ alkyl a hydroxylated $C_{1-4}$ alkyl, phenoxy and an ether; and X is represented by hydrogen or a $C_{1-4}$ alkyl.

The preferred (−) 2-substituted-ornithines of Formula I above, are those wherein R is represented by a $C_{1-4}$ alkyl, $C_{1-4}$ alkoxy, or a halogenated $C_{1-4}$ alkyl and X is represented by hydrogen. The most preferred (−) 2-substituted-ornithines are those wherein R is a methylene radical substituted with one or two halogen atoms and X is hydrogen. Representative examples of preferred (−) 2-substituted-ornithines include 2-fluoromethylornithine, 2-difluoromethylornithine, 2-chloromethylornithine, and 2-dichloromethylornithine.

The starting material in the process of the present invention is a 2-substituted piperidone of the formula:

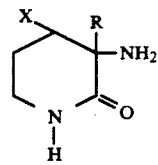

wherein R and X are as defined above.

The 2-substituted-piperidone utilized as the starting material should contain substituents which are analogous to those in the desired 2-substituted-ornithines. For example if the desired (−) 2-substituted-ornithine is 2-difluoromethylornithine, then in the piperidone which is utilized, R should be represented by a difluoromethyl substituent and X should be hydrogen.

Methods for producing these 2-substituted piperidones are known in the art. The Bey, et al. article discussed above discloses such methods.

The stereochemical orientation of the 2-substituted piperidone can be important. Only those 2-substituted piperidones having an (−) orientation will serve as a substrate for the L-α-amino-E-caprolactam hydrolase. Thus in a racemic mixture of 2-substituted-piperidones, the (−) piperidones will be hydrolyzed into the desired (−) ornithines, while the (+) piperidones will not be hydrolyzed to a significant extent.

The enzyme, L-α-amino-E-caprolactam hydrolase is known in the art. Fukmura, et al. in *FEBS Letters*, Vol. 89, number 2, pages 298–300 (1978) discloses methods for producing, recovering, and purifying the enzyme. The enzyme L-α-amino-E-caprolactam is produced by the fungus designated as *Cryptococcus laurentii* Toray 2001. This culture is on deposit in Japan at the Fermentation Research Institute and is designated as FERM P-709. In addition, FERM P-709 is cross-referenced and is available in the American Tissue Culture Collection under the designation ATCC 36832.

It is not necessary that the enzyme be pure prior to its utilization in the present invention. The L-α-amino-E-caprolactam hydrolase present in a crude extract or in a partially purified sample can be utilized. As is apparent those skilled in the art, the recovery and purification of the final product is simplified as the purity of the enzyme preparation utilized is increased.

An enzymatically effective amount of the L-α-amino-E-caprolactam hydrolase should be present during the hydrolysis. This amount can vary widely depending upon the quantity of substrate present and the time in which it is desired to complete the hydrolysis. We have discovered that about 1 mg of enzyme (pure) will hydrolyse about 0.2 micro- moles of the 2-substituted piperidone in 1 minute. Thus, one of ordinary skill in the art can select an enzymatically effective amount depending upon the time in which he desires to complete the reaction.

The L-α-amino-E-caprolactam hydrolase is typically contacted with the 2-substituted-piperidone in the presence of a divalent cation. Representative examples of suitable divalent cations include Mg, Mn, Zn. The quantity of divalent cation which is utilized can also vary widely. Generally though, the divalent cation will be present in a quantity of from about 0.1 moles to about 0.001 moles for every mole of piperidone utilized. The particular anion which is associated with the cation is not critical.

The hydrolysis of the 2-substituted-piperidone is typically conducted in the presence of a buffer capable of maintaining the reaction zone within a pH range of about 7 to about 11, and more preferably about 8 to about 10. Typically the buffer will be present in a concentration of from about 0.1 molarity to about 1 molarity. Representative examples of suitable buffers include tris chloride, alkanolamines, borates, alkylene diamines, and bicarbonates. Relatively volatile alkanolamine buffers such as N,N-dimethyl aminoethanol present in a molarity of about 0.2 are currently preferred.

It is preferred that the hydrolysis be conducted at a temperature range of from about 10° C. to about 50° C., and more preferably from about 20° C. to about 30° C. The hydrolysis is typically allowed to proceed for a period of time ranging from about 20 hours to about 100 hours before the (−) 2-substituted-ornithine is recovered, and more preferably from about 20 hours to about 40 hours.

The (−) 2-substituted-ornithine can be recovered and purified by techniques known in the art. One such technique comprises extracting the reaction zone with an organic solvent such as chloroform, separating and concentrating the resulting aqueous layer and then obtaining the desired ornithine by recrystallization from a solvent system such as water/ethanol. Other suitable solvent systems will be readily apparent to those skilled in the art.

A preferred manner for recovering and purify the (−) 2-substituted-ornithine is the following reaction scheme. First the reaction mixture is heated to a temperature range of about 60° C. to about 100° C., preferably about 90° C.–100° C. for a period of time ranging from about 0.1 hours to about 20 hours, preferably about 1 hour. At that point, activated charcoal is stirred with the heated mixture for a period of time ranging from about 1 minute to about 10 minutes and then the mixture is filtered. The filtrate is concentrated to a solid state. The solid is dissolved in water, extracted with an organic solvent such as chloroform. The desired ornithine will be found in the aqueous phase, while the unreacted piperidone will be found in the organic phase. If desired this unreacted piperidone can be recovered and utilized for other purposes.

The aqueous layer is then reconcentrated and washed with an alcohol, such as isopropanol. The resulting mixture is then subjected to ion exchange chromatography on a anionic exchange column utilizing ammonium hydroxide as the eluant. The resulting eluant can then be concentrated to dryness to obtain the desired (−) 2-substituted-ornithine. If a acid salt of the ornithine is desired, then it can be obtained by acidifying the eluant with the appropriate acid prior to concentration. Analytically pure samples can be obtained by conducting an additional recrystallization in aqueous ethanol.

The unreacted piperidone can be obtained by concentrating the organic extract obtained from either purification technique and subjecting the resulting concentrate to recrystallization in a chloroform/hexane solvent system. This piperidone mixture contains predominantly the d isomer along with any of the unreacted l isomer.

The following examples are presented to further demonstrate the process of the present invention. However, they should not be construed as limiting the scope of the invention in any manner.

EXAMPLE I

To a solution of 150 mg of crude enzyme extract (containing therein 0.75 mg of L-α-amino-E-caprolactam hydrolase, and 1 ml of 1 molar $MnCl_2$ in 6.0 ml of 0.2M tris chloride buffer (pH 8.5) was added 250 mg of DL-2-amino-2-difluoromethylpiperidone. The resulting mixture was stirred at room temperature for 48 hours and then was extracted 3 times with 10 ml of chloroform.

The resulting aqueous layer was separated, acidified with 6N HCl and concentrated to dryness in a stream of nitrogen. The resulting concentrate was recrystallized from water-ethanol and 36.0 mg of difluoromethylornithine was obtained.

A sample of the aqueous layer was analyzed by HPLC on a chiral column and it was determined that the ratio of l-isomer to d-isomer was 46:1. The combined chloroform layers were dried with magnesium sulfate, filtered, and concentrated to dryness. After one recrystallization from chloroform-pentane, 120.8 mg of the unreacted (+) piperidone (80% optical purity) was recovered.

EXAMPLE II

L-α-amino-E-caprolactam hydrolase (1.8 gm) and 7.2 ml of 0.001M MnCl$_2$ were added to 72 ml of N,N-dimethyl aminoethanol buffer (0.22 M, pH 8.5) and the resulting mixture was stirred for 5 minutes. 3.0 g of DL-2-amino-2-difluoromethylpiperidone was added to this mixture and stirred at ambient temperature for about 40 hours. The mixture was then heated at 90° C. for one hour. 3.0 g of activated charcoal was then added and the resulting mixture was stirred for 5 minutes. The mixture was then filtered and the filtrate was concentrated in vacuo to dryness. The solid was dissolved in 2 ml of water and the clear mixture was extracted with chloroform (3×15 ml).

The resulting aqueous layers were combined, washed with isopropanol, and subjected to ion exchange chromatography using a anionic resin such as Dowex 500 with NH$_4$OH as the eluant. The resulting eluant was acidified to a pH of 2 and then concentrated to dryness yielding 1.15 g of (−) 2-difluoromethylornithine representing a yield of 80% based on the (−) piperidone starting material, having an optical purity of >92%.

What is claimed is:

1. A process for the production of (−)-2-difluoromethylornithine comprising:
   a) contacting a 2-substituted piperidone of the formula:

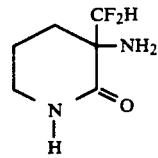

with an enzymatically effective amount of L-α-amino-E-caprolactam hydrolase obtained from the fungus *Cryptococcus laurentii* Toray 2001 in the presence of a divalent metal cation selected from the group consisting of zinc, manganese, and magnesium, and
   b) recovering the (−)-2-difluoromethylornithine produced.

2. The process of claim 1 wherein said divalent metal cation is present in the quantity of from about $10^{-1}$ to about $10^{-3}$ moles for every mole of 2-substituted piperidone present.

3. The process of claim 2 wherein said hydrolysis is conducted in a buffer capable of maintaining a pH within the range of about 8 to about 10.

4. The process of claim 3 wherein said hydrolysis is conducted at a temperature range of from about 20° C. to about 30° C.

* * * * *